United States Patent [19]

Martel et al.

[11] Patent Number: 4,720,556
[45] Date of Patent: Jan. 19, 1988

[54] 3-OXABICYCLO-(3,1,0)-HEXAN-2-ONES

[75] Inventors: Jacques Martel, Bondy; Jean Tessier, Vincennes; André Teche, Nanterre, all of, France

[73] Assignee: Roussel Uclaf, Paris, France

[21] Appl. No.: 930,770

[22] Filed: Nov. 14, 1986

Related U.S. Application Data

[60] Division of Ser. No. 745,653, Jun. 17, 1985, Pat. No. 4,658,043, which is a division of Ser. No. 447,442, Dec. 6, 1982, Pat. No. 4,540,797, which is a continuation of Ser. No. 253,869, Apr. 13, 1981, abandoned, which is a division of Ser. No. 21,833, Mar. 19, 1979, Pat. No. 4,265,817.

[30] Foreign Application Priority Data

Mar. 17, 1978 [FR] France ............... 78 07778

[51] Int. Cl.$^4$ ........................... C07D 307/93
[52] U.S. Cl. ...................................... 549/302
[58] Field of Search .......................... 549/302

[56] References Cited

U.S. PATENT DOCUMENTS 4,132,717 1/1979 Roman ........................... 549/302

FOREIGN PATENT DOCUMENTS 1935386 1/1970 Fed. Rep. of Germany ...... 549/302

*Primary Examiner*—Jane T. Fan
*Attorney, Agent, or Firm*—Bierman & Muserlian

[57] ABSTRACT

Novel ethers of organic compounds containing chiral atoms of the formula

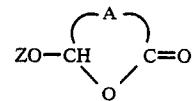

wherein A is a hydrocarbonated chain of 1 to 10 groups, the said chain containing one or more heteroatoms, one or more unsaturations, the assembly of the groups constituting the chain may represent a mono- or polycyclic system, including a system of the spiro or endo type, the chain A can contain one or more chiral atoms or the lactone moiety can present a chirality due to the dissymetric spatial configuration of the whole of the molecule and Z is selected from the group consisting of primary, secondary or tertiary alcohol moiety containing at least an asymetric carbon atom, a phenol moiety substituted comprising at least one asymetric carbon atom and an substituted alcohol or phenol moiety with a chirality due to the dissymetric spatial configuration of the whole of the molecule, with the proviso Z is not (R) or (S) α-cyano-3-phenoxy-benzyl when A is

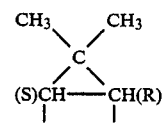

which are useful for the resolution of compounds of the formulae

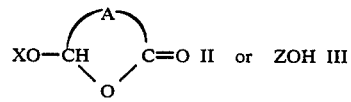

wherein A and Z have the above definitions and X is selected from the group consisting of hydrogen and alkyl of 1 to 4 carbon atoms.

1 Claim, No Drawings

3-OXABICYCLO-(3,1,0)-HEXAN-2-ONES

PRIOR APPLICATION

This application is a division of U.S. patent application Ser. No. 745,653 filed June 17, 1985 now U.S. Pat. No. 4,658,043 issued 4/14/87 a division of copending patent application Ser. No. 447,442 filed Dec. 6, 1982, now U.S. Pat. No. 4,540,797 which is a continuation of application Ser. No. 253,869 filed Apr. 13, 1981, now abandoned, which in turn is a division of our application Ser. No. 21,833 filed Mar. 19, 1979, now U.S. Pat. No. 4,265,817.

OBJECTS OF THE INVENTION

It is an object of the invention to provide the novel products of formula I and to provide a novel process for their preparation.

It is another object of the invention to provide a novel process for the resolution of compounds of formulae II or III.

These and other objects and advantages of the invention will become obvious from the following detailed description.

THE INVENTION

The novel ethers of the invention having an organic group comprising chiral atoms are comprised of compounds of the formula

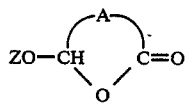
I wherein A is a hydrocarbonated chain of 1 to 10 groups, the said chain containing one or more heteroatoms, one or more unsaturations, the whole of the groups constituting the chain may represent a mono- or polycyclic system including a system of the spiro or endo type, the chain A can contain one or more chiral atoms or the lactone moiety can present a chirality due to the dissymetric spatial configuration of the whole of the molecule and Z is selected from the group consisting of primary, secondary or tertiary alcohol moiety containing at least one asymetric carbon atom, a phenol moiety substituted comprising at least one asymetric carbon atom and an substituted alcohol or phenol moiety with a chirality due to the dissymetric spatial configuration of the whole of the molecule, with the proviso Z is not (R) or (S) αcyano-3-phenoxy-benzyl when A is

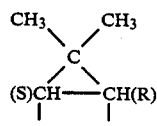

Among the compounds of formula I are those wherein the A chain contains one or more asymetric carbon atoms and the chemical structure imposes by the hydroxylan unequivocally spatial disposition. In this type of compound, the two different atoms or radicals which are substituted on the carbon atoms of the chain are selected from at least one member of the groups consisting of (a) hydrogen, halogen, nitro, alkyl of 1 to 10 carbons atoms, cycloalkyl of 3 to 6 carbon atoms and phenyl optionally substituted with at least one member of the group consisting of halogen, alkyl, alkoxy and alkylthio of 1 to 6 carbon atoms, carboxyl, —CN, —CHO,

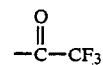

and acyl of an organic carboxylic acid of 1 to 10 carbon atoms, (b) —NH—$R_1$ wherein $R_1$ is selected from the group consisting of hydrogen, alkyl of 1 to 6 carbon atoms, benzoyl,

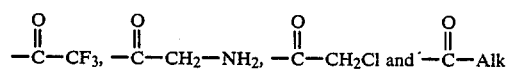

wherein AlK is alkyl of 1 to 6 carbon atoms and

(c)

wherein $R_2$ and $R_3$ are individually alkyl of 1 to 6 carbon atoms, or $R_2$ is carboxyl and $R_3$ is benzyl or $R_2$ and $R_3$ together with the nitrogen atom to which they are attached form a 6-member heterocycle.

Among the particularly interesting families of compounds of formula I are those wherein A is an aliphatic hydrocarbon chain of 2 to 3 carbon atoms, those wherein A is an aliphatic hydrocarbon chain interrupted with a heteroatom, those wherein A is an aliphatic hydrocarbon chain containing a double bond, those wherein A is monocyclic hydrocarbon chain of 3 to 6 carbon atoms optionally containing one unsaturation, and those wherein A is a bicyclic hydrocarbon chain of 5 to 10 carbon atoms optionally containing one unsaturation.

Particularly preferred compound of formula I are those wherein A has the formula

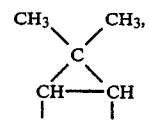

those wherein A has the formula

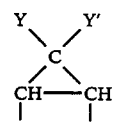

and Y and Y' are individually selected from the group consisting of hydrogen, chlorine, fluorine, bromine and alkyl of 2 to 6 carbon atoms or Y and Y' together with the carbon to which they are attached form a carbon homocycle of 3 to 7 carbon atoms, those wherein A has the formula

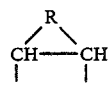

and R is selected from the group consisting of —O—, —S—, —NH— and —NR'— and R' is alkyl of 1 to 6 carbon atoms, those wherein Z has the formula

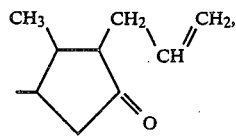

and those wherein Z has the formula

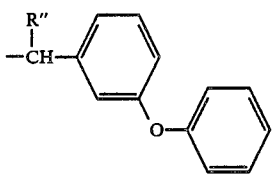

and R" is selected from the group consisting of alkyl of 1 to 6 carbon atoms, alkenyl of 2 to 6 carbon atoms, alkynyl of 2 to 6 carbon atoms and —CN.

In the compounds of formula I, the group Z is derived from an alcohol which may be aliphatic, cycloaliphatic or aromatic, mono or polycyclic, primary, secondary or tertiary alcohol. Among the preferred alcohols are the cyanohydrins. Z may equally be derived from a phenol substituted with one or more substituents containing at least one asymetric carbon atom.

Among the specific preferred compounds or mixtures of compounds of formula I are a mixture of (1R,5S) 6,6-dimethyl-4(R)-[1(S)-2-methyl-4-oxo-3-(2-propen-l-yl)-cyclopent-2-enyloxy]-3-oxabicyclo-(3,1,0,)-hexan-2-one and (1R,5S) 6,6-dimethyl-4-(R)-[1(R)-2-methyl-4-oxo-3-(2-propen-l-yl)-cyclopent-2-enyloxy]-3-oxabicyclo-(3,1,0)-hexan-2-one, a mixture of (1S,5R) 6,6-dimeth yl-4(R)-[1(S)-2-methyl-4-oxo-3-(2-propen-l-yl)-cyclopent-2-enyloxy]-3-oxabicyclo-(3,1,0)-hexan-2-one and (1S,5R) 6,6-dimethyl-4(R)-[1(R)-2-methyl-4-oxo-3-(2-propen-l-yl)-cyclopent-2-enyloxy]-3-oxabicyclo-(3,1,0)-hexan-2-one, (1R,5S) 6,6-dimethyl-4(R)-[1(S)-2-methyl-4-oxo-3-(2-propen-l-yl)-cyclopent-2-enyloxy]-3-oxabicyclo-(3,1,0)-hexan-2-one, (1S,5R) 6,6-dimethyl-4(R)-[1(R)-2-methyl-4-oxo-3-(2-propen-l-yl)-cyclopent-2-enyloxy]-3-oxabicyclo-(3,1,0)-hexan-2-one, (1R,5S) 6,6-dimethyl-4(R)-[3',3'-dimethyl-butyrolactone-2'(S)-oxy]-3-oxabicyclo-(3,1,0)-hexan-2-one, (1R,5S) 6,6-dimethyl-4(R)-(3',3'-dimethyl-butyrolactone-2'(R)-oxy]-3-oxabicyclo-(3,1,0)-hexan-2-one, mixtures of the said butyrolactones, (3R, 3aR, 4S, 7R, 7aS) 3-[(1'R), (2'S), (5'R) 2'-isopropyl-5'-methyl cyclohexanoxy]-tetrahydro-4,7-methanoisobenzofuran-1-one, (3R, 3aR, 4S, 7R, 7aS) 3-[(1'S), (2'R), (5'S) 2'-isopropyl-5'-methyl-cyclohexanoxy]-tetrahydro-4,7-methano-isobenzofuran-1-one, mixtures of the last two compounds, (1R,5S) 6,6-dimethyl-4(R)-[(1'R), (2'S), (5'R) 2'-isopropyl-5'-methyl-cyclohexanoxy]-3-oxabicyclo-(3,1,0)-hexan-2-one, (1R,5S) 6,6-dimethyl-4(R)-[(1'S), (2'R), (5'S) 2'-isopropyl-540 -methyl-cyclohexanoxy]-3-oxabicyclo-(3,1,0)-hexan-2-one and mixtures of the last two compounds.

The novel process of the invention for the preparation of compound of formula I comprises reacting a lactonic compound of the formula

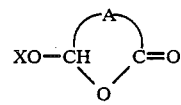   II wherein A has the above definition and X is selected from the group consisting of hydrogen and alkyl of 1 to 4 carbon atoms in the presence of an acid with a substituted phenol or alcohol of the formula

Z—OH   III wherein Z has the above definition to obtain either a compound of the formula

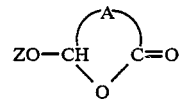   I$_A$ wherein the chiral atoms possess a well defined configuration when the lactone and the alcohol or phenol posses one or more chiral atoms of well defined configuration, or a mixture of diastereoisomers named I$_B$ when the lactone is a well defined optical isomer and the chiral centers of the alcohol or phenol do not have an unequivocal configuration, or a mixture of diastereoisomers named I$_C$ when the alcohol or phenol is a well defined optical isomer and the chiral atoms of the lactone do not have an unequivocal configuration and then separating by physical methods the diastereoisomeric ethers contained either in the mixtures of type I$_B$ or mixtures of type I$_C$ and notably the ethers of formula I$_A$ whose chiral centers are of an unquivocal configuration.

The acid agent in whose presence the reaction of the phenol or alcohol with the lactone is effected may be selected from the group consisting of sulfonic acids, perchloric acid and 5-sulfosalicyclic acid. The water of reaction or the alcohol formed is preferably removed by azeotropic distillation at reflux in an organic solvent such as chlorinated solvents, aromatic or aliphatic hydrocarbons or ethers, but the reaction may be effected in the absence of a solvent under reduced pressure. The physical separation of the diastereoisomeric ethers is preferably effected by crystallization or chromatography.

If the one or more chiral atoms of the lactonic copule II are each of (R) or (S) determined steric configuration, when one or more of asymetric carbon atoms of the substituded alcohol or phenol III are also individually of (R) or (S) determined steric configuration, there is directly obtained with retention of configuration the compounds of formula I corresponding to those of formula I$_A$. When in the process, the substituted alcohol or phenol III possesses one or more non-resolved asymetric carbon atoms, there is obtained a mixture of diastereoisomeric ethers I denominated as formula I$_B$ which may then be separated by a physical treatment such as chromatography or crystallization from a solvent. The latter case is particularly interesting.

After separation of the formed diastereoisomeric ethers of formula $I_B$, for example after separation of a compound of formula $I_A$, a simple hydrolysis or alcoholysis such as indicated above, permits the obtention of resolved substituted alcohols or phenols on a level of 5 from the initial racemic asymetric carbon atoms. When the substituted alcohol or phenol possesses M non-resolved chiral centers, there are formed 2 M diastereoisomers similar to $I_A$ which convenient can be separated into individual of formula $I_A$. One may recover by another way the lactonic compound of formula II where the chiral atoms are of (R) or (S) determined steric configuration which exist starting from the compounds of formula II.

In an analogous fashion in the process of the preparation of the compounds of formula I, if one or more asymetric carbon atoms of the substituted alcohols or phenols of formula III are (R) or (S) determined steric configurations, when one or more chiral atoms of the lactonic copule are also (R) or (S) determined steric configuration, one obtains directly with retention of the configuration the corresponding compounds indicated as $I_A$.

When in the process, the lactonic couple has the (R,S) racemic configuration due to one or more unresolved chiral centers, there is obtained a mixture of diastereoisomeric ethers of formula I designated as $I_C$ which may be separated by physical means, especially chromatography or crystallization from a solvent, with the latter being particularly interesting.

After separation of the formed diastereoisomeric ethers $I_C$, for example after separation of $I_A$, a simple hydrolysis or alcoholysis as indicated above permits the obtaining of resolved lactonic compound on the level of the chiral atoms of (R,S) racemic configuration in the initial mixture. When the lactonic couple possess n unresolved chiral centers, there are formed 2n diastereoisomers looking like $I_A$ which eventually can be separated into individual like $I_A$.

Another way, the utilized substituted alcohol or phenol III is recovered of which the asymetric carbon atoms have the (R) or (S) determined steric configuration as in the starting compound ZOH.

In all of the preceding discussion, the presence of one or more resolved or non-resolved chiral centers in compounds II or III imply the following different possibilities: either one of the chiral centers possesses an unequivocal (R) or (S) configuration and the molecule is then a mixture of racemic groups of enantiomers or one part of the chiral centers possesses an unequivocal (R) or (S) configuration and the molecule is then a mixture of diastereoisomers or all the chiral centers have an unequivocal (R) or (S) configuration and then the molecule is considered to be a well defined optical isomer.

Besides the asymetry due to the presence of chiral centers in the molecule of compounds II or III, they can have a geometric isomerism due to the presence of one or more (E) or (Z) double bonds so that a supplemental chirality due to the spatial conformation of the ensembly of the molecule of which the atoms constituting it is able, for example, to divide into 2 orthogonal planes. The process of the invention equally applies in this case and one is still able to effect a resolution of one or more racemic asymetrical carbon atoms presented in a copule of ether I thanks to the chirality of the other part of ether I.

The invention has as its subject, preferably, a process for the preparation of compounds of formula I comprising in that compound II is the lactone of a racemate or an optical isomer of cis 2,2-dimethyl-3-(dihydroxymethyl)-cyclopropane-1-carboxylic acid and compound III is an optical isomer or racemate of 1-hydroxy-2-methyl-3-(2-propen-1-yl)-cyclopent-2-en-4-one and the resulting diastereoisomeric compound I is separated by crystallization from an organic solvent. Another preferred process of the invention comprises reacting the lactone of a racemate or optical isomer of cis 2,2-dimethyl-3-(dihydroxymethyl)-cyclopropane-1-carboxylic acid and a racemate or optical isomer of 2-hydroxy-3,3-dimethyl-butyrolactone or pantolactone and the resulting diastereoisomeric compound I is separated by chromatography. Another process of the invention comprises reacting a racemate or optical isomer of 3-hydroxy-tetrahydro-4,7-methano-isobenzofuran-1-one with a racemate or optical isomer of menthol and the resulting diastereoisomeric compound I is separated by chromatography. A further process of the invention comprises reacting the lactone of a racemate or an optical isomer of cis 2,2-dimethyl-3-(dihydroxymethyl)-cyclopropane-1-carboxylic acid and a racemate or optical isomer of menthol and the resulting diastereoisomeric compound is separated by chromatography.

The process of the invention for the resolution of compounds of formulae II or III with a compound of formula I comprises reacting a compound of the formula

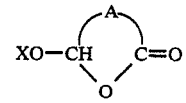     II wherein X is selected from the group consisting of hydrogen and alkyl of 1 to 4 carbon atoms and A has the above definition in the presence of an acid with an substituted alcohol or phenol of the formula

ZOH     III wherein Z has the above definition to obtain either a mixture of diastereoisomers designated $I_B$ when the lactone is a well defined optical isomer and the chiral centers of the alochol or phenol do not have an unequivocal configuration or a mixture of diastereoisomers designated $I_C$ when the alcohol or phenol is a well defined optical isomer and the chiral atoms of the lactone do not have an unequivocal configuration, separating by physical methods the diastereoisomeric ethers contained in mixtures $I_B$ or $I_C$ to obtain particularly ether designated $I_A$ in which the chiral centers have an unequivocal configuration and subjecting each of the so separated ethers to hydrolysis or an alcoholysis in an acid medium to obtain either a compound of type II and the other diastereoisomers eventually arising due to the existence of more asymetric centers or a compound of type III and the other diastereoisomers eventually arising due to the existence of more asymetric centers, those compounds of formulae II and III and the corresponding diverse diastereoisomers, containing chiral centers of unequivocal configuration, in other words the resolved chiral centers due to the corresponding chiral centers of the starting phenols or alcohols or due to the chiral centers of the starting lactone compounds.

The acid solvolysis of compounds of Type $I_A$ (diastereoisomers of unequivocal configuration) which results from the diastereoisomer mixtures $I_B$ or $I_C$ permits the obtention of the alcohol or phenol of formula III as well as the lactone of formula II, each in its optical isomer form, that is to say all the configuration of the chiral centers are exactly defined as (R) or (S).

By the application of this process in which the starting alcohol which comprises a single chiral center is a racemate formed by 2 antipodes (R) and (S) one can, by opposing it with a well defined optical isomer of lactone II, obtain 2 ethers of the Type $I_A$ named respectively $I_D$ and $I_E$ than can be separated by a physical treatment, especially by crystallization or chromatography. In the compounds $I_D$ and $I_E$, the alcohol moiety presents an antipodal configuration. By acid solvolysis of either $I_D$ or $I_E$, one can recover the alcohol ZOH resolved into its antipodes (R) and (S), respectively.

By starting with a lactone having chiral centers presenting configurations corresponding to a racemate and being opposed with a well defined optical isomer of an alcohol or phenol of formula III, one also obtain 2 ethers of type $I_A$ named $I_F$ and $I_G$, respectively, which can be separated by physical methods, especially by chromatography or crystallization. In the compounds $I_F$ and $I_G$, the lactone moiety presents an antipodal configuration and acid solvolysis of either $I_F$ or $I_G$ results in the lactone II resolved into its two antipodes.

A preferred process of the invention comprises reacting the lactone of cis 2,2-dimethyl-3S-(dihydroxymethyl)-cyclopropane-1R-carboxylic acid in the presence of an acid agent with 1(RS)-hydroxy-2-methyl-3-(2-propen-1-yl)-cyclopent-2-en-4-one to obtain a mixture of (1R,5S) 6,6-dimethyl-4(R)-[1(R)-2-methyl-4-oxo-3-(2-propen-1-yl)-cyclopent-2-enyloxy]-3-oxabicyclo-(3,1,0)-hexan-2-one and (1R,5S) 6,6-dimethyl-4(R)-[1(S)-2-methyl-4-oxo-3-(2-propen-1-yl)-cyclopent-2-enyloxy]-3-oxabicyclo-(3,1,0)-hexan-2-one, crystallizing the 1(S) isomer from isopropanol and subjecting the 1(S) isomer to acid solvolysis to obtain 1(S)-hydroxy-2-methyl-3-(2-propen-1-yl)-cyclopent-2-en-4-one. The 1R isomer may also be subjected to acid solvolysis to obtain 1(R)-hydroxy-2-methyl-3-(2-propen-1-yl)-cyclopent-2-en-4-one. The acid solvolysis is preferrably effected in an aqueous medium in the presence of hydrochloric acid or in methanol in the presence of p-toluene sulfonic acid.

Another modification of the process of the invention comprises reacting in the presence of an acid agent the lactone of dl cis 2,2-dimethyl-3-(dihydroxymethyl)-cyclopropane-1-carboxylic acid with 1(S)-hydroxy-2-methyl-3-(2-propen-1-yl)-cyclopent-3-en-4-one to form a mixture of (1R, 5S) 6,6-dimethyl-4(S)-[1(S)-2-methyl-4-oxo-3-(2-propen-1-yl)-cyclopent-2-enyloxy]-3-oxabicyclo-(3,1,0)-hexan-2-one and (1R, 5S) 6,6-dimethyl-4(R)-[1(S)-2-methyl-4-oxo-3-(2-propen-1-yl)-cyclopent-2-enyloxy]-3-oxabicyclo-(3,1,0)-hexan-2-one crystallizing the 4(S) isomer from isopropyl ether and subjecting the latter to acid solvolysis to obtain the lactone of cis 2,2-dimethyl-3S-(dihydroxymethyl)-cyclopropane-1R-carboxylic acid. The preferred acid agent is hydrochloric acid.

Another mode of the process comprises reacting the lactone of cis 2,2-dimethyl-3S-(dihydroxy-methyl)-cyclopropane-1R-carboxylic acid in the presence of an acid agent with 2(R,S)-hydroxy-3,3-dimethyl-butyrolactone to obtain a mixture of (1R,5S) 6,6-dimethyl-4(R)-[3',3'-dimethylbutyro-lactone-2'(S)-oxy]-3-oxabicyclo-(3,1,0)-hexan-2-one and (1R, 5S) 6,6-dimethyl-4(R)-[3',3'-dimethylbutyrolactone-2'(R)-oxy]-3-oxybicyclo-(3,1,0)-hexan-2-one, separating the isomers by chromatography and subjecting one or the other isomer to acid solvolysis to obtain either 2(S)-hydroxy-3,3-dimethylbutyrolactone or 2(R)-hydroxy-3,3-dimethylbutyrolactone from the 2'(S) or 2'(R) ether, respectively. Preferably, the acid solvolysis is effected with p-toluene sulfonic acid in an aqueous medium or methanol.

An additional modification of the process of the invention comprises reacting (3R, 3aR, 4S, 7R, 7aS) 3-hydroxy-tetrahydro-4,7-methano-isobenzofuran-1-one with (R,S) menthol in the presence of an acid agent to obtain a mixture of (3R, 3aR, 4S, 7R, 7aS) 3-[(1'R), (2'S), (5'R) 2'-isopropyl-5'-methyl-cyclohexanoxy]-tetrahydro-4,7-methano-isobenzofura-1-one and (3R, 3aR, 4S, 7R, 7aS) 3-[(1'S), (2'R), (5'S) 2'-isopropyl-5'-methyl-cyclohexanoxy]-tetrahydro-4,7-methanoisobenzofuran-1-one, separating the said isomers by chromatography and subjecting one or the other isomer to acid solvolysis to obtain (R) or (S) menthol.

Another preferred modification of the process of the invention comprises reacting the lactone of cis 2,2-dimethyl-3S-(dihydroxymethyl)-cyclopropane-1R-carboxylic acid in the presence of an acid agent with (R,S)-menthol to obtain a mixture of (1R, 5S) 6,6-dimethyl-4(R)-[(1'R), (2'S), (5'R) 2'-isopropyl-5'-methyl-cyclohexanoxy]-3-oxabicyclo-(3,1,0)-hexan-2-one and (1R, 5S) 6,6-dimethyl-4(R)-[(1'S), (2'R), (5'S) 2'-isopropyl-5'-methyl-cyclohexanoxy]-3-oxabicyclo-(3,1,0)-hexan-2-one, separating the said isomers by chromatography and subjecting one or the other of the isomers to acid solvolysis to obtain either (R) or (S)-menthol. The solvolysis is preferably effected with p-toluene sulfonic acid in an aqueous medium.

There are a few known general procedures for the resolution of alcohols containing asymetric carbon atoms. For example, it is known to react certain (R,S) racemic alcohols with an optically active organic acid and then to separate by any convenient physical method the ester of the (S) alcohol and the ester of the (R) alcohol and to subject the individual esters of hydrolysis to obtain the alcohol of (R) or (S) structure.

A more complicated resolution process is also known where the (R,S) racemic alcohol is reacted with an organic diacid to obtain a mixture of hemiesters which is then reacted with an optically active base to separate the corresponding diastereoisomeric salts, subjecting the said individual salts to acidification to obtain the hemiesters of the (S) alcohol and of the (R) alcohol and subjecting the individual hemiesters of hydrolysis to recover the alcohol of (R) or of (S) configuration.

However, these types of resolution can only be applied without difficulty to sufficiently stable alcohols, insensible or slightly insensible to conditions of formation and hydrolysis of the intermediate esters or hemiesters.

The process of the present invention provides a novel, very general method of resolutin of substituted alcohols or phenols of formula III containing one or more asymetrical carbon atoms which method does not have the inconveniences of the prior art methods. This novel method using the diverse steps discussed above consists of reacting the substituted alcohol or phenol of formula III containing at least one asymetrical carbon atoms of (R,S) configuration in the presence of an acid agent with an optical isomer of a lactone of formula II possessing one or more chiral atoms of well definite steric configuration (R) or (S) to obtain an equimolar mixture of diastereoisomers of type $I_A$ in which the radical (Z) possesses an unequivocal stereochemistry due to each chiral center. The diastereoisomers of type $I_A$ may be separated by physical methods such as chromatography or crystallization from a solvent and then subjecting the individual diastereoisomers of type $I_A$ to solvolysis in an acid medium to obtain, respectively, the substituted alcohol or phenol of formula III with an unequivocal stereochemistry.

This method has the advantage over other known resolution methods of greater simplicity than the prior art in the steps of reacting the substituted alcohols or phenols of formula III with the lactone of formula II which is used in the form of an optical isomer of determined stereochemistry to obtain the corresponding diastereoisomeric ethers of type $I_B$ which are separated by physical methods into compounds of type $I_A$ which have a well defined stereochemistry and then subjecting each of the compounds of type $I_A$ to acid solvolysis to obtain the resolved substituted alcohols or phenols of formula III.

The resolution method of the invention has a very general application since the reaction of the compound of formula III with an optical isomer of formula II is effected in very good yields and the resulting ethers generally possess a structure wherein the separation by physical means of stereoisomers of type $I_A$ is easy. The separation may be effected by crystallization from any convenient solvent and the solvolysis of the diastereoisomers of type $I_A$ in acid media leads without difficulty and in good yields to the resolved substituted alcohols or phenols of formula III.

The final solvolysis may be effected without any notable alteration of the compound of formula III and the stereochemistry of the compounds of formula II is maintained during the solvolysis only if the structure of the compound of formula II imposes to the hydroxylan unequivocal disposition. The resolution process of the invention is especially useful for extremely fragile or sensitive alcohols such as cyanhydrins.

This method of resolution of substituted alcohols or phenols generally is widely used to permit obtaining in the majority of cases and under advantageous conditions starting from racemic compounds obtained by chemical synthesis, the resolved optical isomers of which one of them generally has the quasi totality of activity of the concerned molecule (case of natural compounds which are optically active).

In the above discussions, it is also a point that there is a new method of resolving lactonic compounds of formula II containing one or more chiral atoms. This new method consists of reacting in the presence of an acid agent a lactone of formula II containing at least one chiral atom of (R,S)racemic configuration with an optical isomer of an substituted alcohol or phenol of formula III of determined steric configuration (R) or (S) to obtain a mixture of diastereoisomeric ethers of type $I_C$, subjecting the said mixture to a physical treatment such as chromatography or crystallization to separate the diastereoisomers of type $I_A$ contained in the mixture, each diastereoisomer presenting in the lactone moiety a well defined stereochemistry, and subjecting these compounds to hydrolysis in an acid media to obtain the compound of formula II in resolved form. This method, which is not described in the literature, presents in a general manner the same advantages and the same simplicity of the resolution of the substituted alcohols or phenols described above.

In the following examples there are described several preferred embodiments to illustrate the invention. However, it should be understood that the invention is not intended to be limited to the specific embodiments.

EXAMPLE 1

Mixture of (1R,5S) 6,6-dimethyl-4(R)-[1(S)-2-methyl-4-oxo-3-(2-propen-1-yl)-cyclopent-2-enyloxy]-3-oxabicyclo-(3,1,0)-hexan-2-one and (1R,5S) 6,6-dimethyl-4(R)-[1(R)-2-methyl-4-oxo-3-(2-propen-1-yl)-cyclopent-2-enyloxy]-3-oxabicyclo-(3,1,0)-hexan-2-one.

A mixture of 3.5 g of p-toluene sulfonic acid, 152 g of (1RS)-hydroxy-2-methyl-3-(2-propen-1-yl)-cyclopent-2-en-4-one, 152 mg of the lactone of cis 2,2-dimethyl-3S-(dihydroxymethyl)-cyclopropane -1R-carboxylic acid and 1000 ml of benzene was refluxed for 4 hours while azeotropically removing the water of reaction and the mixture was cooled to 20° C. The pH of the mixture was adjusted to 7-8 by addition of triethylamine and the mixture was evaporated to dryness under reduced pressure to obtain a mixture of (1R,5S) 6,6-dimethyl-4(R)-[1(S)-2-methyl -4-oxo-3-(2-propen-1-yl)-cyclopent-2-enyloxy]-3-oxabicyclo(3,1,0)-hexan-2-one and (1R,5S) 6,6-dimethyl-4(R)-[1(R)-2-methyl-4-oxo-3-(2-propen-1-yl)-cyclopent-2-enyloxy]-3-oxabicyclo-(3,1,0)-hexan-2-one.

EXAMPLE 2

(1R,5S) 6,6-dimethyl-4-(R)-[1(S)-2-methyl-4-oxo-3-(2-propen-1-yl)-cyclopent-2-enyloxy]-3-oxabicyclo-(3,1,0)-hexan-2-one The mixture of Example 1 was added to 300 ml of isopropanol and the mixture was stirred at 0° C. and was then vacuum filtered. The recovered product was washed and dried to obtain 82.6 g of (1R,5S) 6,6-dimethyl-4-(R)-[1-(S)-2-methyl-4-oxo-3-(2-propen-1-yl)-cyclopent-2-enyloxy]-3-oxabicyclo-(3,1,0)-hexan-2-one melting at 104° C. and having a specific rotation of $[\alpha]_D 20= -66.5°$ C. (c=1.1% in benzene).

Analysis: $C_{16}H_{20}O_4$; molecular weight=276, Calculated: %C 69.54, %H 7.3, Found: %C 69.3, %H 7.4.

Circular dichroism (dioxane): $\alpha\epsilon = -26.4$ at 222 nm (max.); $\alpha\epsilon = +2.8$ at 321 nm (max); $\alpha\epsilon = +2.50$ at 332 nm (max.).

RMN Spectrum (deuterochloroform): peaks at 1.22 ppm (hydrogen of geminal methyls); at 1.97 to 2.33 ppm (hydrogens of cyclopropane ring); at 2.1 ppm (hydrogens of 2-methyl of allethrolone); at 2.92–3.02 ppm (1-methylene of allyl of allethrolone); at 4.63 ppm (1-hydrogen of allethrolone); at 4.75–5.17 ppm (hydrogens of terminal methylene in 3-position of allyl of allethrolone); at 5.33 ppm (hydrogen on carbon α to endocyclic oxygen); at 5.47–6.16 ppm (2-hydrogen of allyl of allethrolone).

EXAMPLE 3

(1R,5S) 6,6-dimethyl-4-(R)-[1(R)-2-methyl-4-oxo-3-(2-propen-1-yl)-cyclopent-2-enyloxy]-3-oxabicyclo-(3,1,0)-hexan-2-one A mixture of 7.5 g of the lactone of cis 2,2-dimethyl-3S-(dihydroxymethyl)-cyclopropane-1R-carboxylic acid, 7.5 g of 1(R)-hydroxy-2-methyl-3-(2-propen-1-yl)- cyclopent-2-ene-4-one, 0.100 g of p-toluene sulfonic acid and 75 ml of benzene was refluxed for 4 hours while the water of reaction was azeotropically distilled off and was then evaporated to dryness under reduced pressure to obtain 15 g of (1R,5S) 6,6-dimethyl-4(R)-[1(R)-2-methyl-4-oxo-3-(2-propen-1-yl)-cyclopent-2-enyloxy]-3-oxabicyclo-(3,1,0)-hexan-2-one.

Circular dichroism (dioxane): $\Delta\epsilon = -2.56$ at 330 nm (max.); $\Delta\epsilon = -2.8$ at 316 nm (max.); $\Delta\epsilon = +14.6$ at 225 nm (max.).

RMN Spectrum (deuterochloroform): peaks at 1.22–1.23 ppm (hydrogens of geminal methyls); at 2.07 ppm (hydrogens of 2-methyl of allethrolone); at 2.92–3.2 ppm (hydrogens of 1-methylene of allyl of allethrolone); at 4.83–5.08 ppm (hydrogens of 3-methylene of allyl of allethrolone); at 4.87 ppm (1-hydrogen of allethrolone); at 5.26 ppm (hydrogen on carbon α to endocyclic oxygen); at 5.47–6.33 ppm (2-hydrogen of allyl of allethrolone).

EXAMPLE 4

(1R,5S) 6,6-dimethyl-4(R)-[1(S)-2-methyl-4-oxo-3-(2-propen-1-yl)-cyclopent 2-enyloxy]-3-oxabicyclo-(3,1,0)-hexan-2-one A mixture of 5 g of the lactone of cis 2,2-dimethyl-3S-(dihydroxymethyl)-cyclopropane-1R-carboxylic acid, 5 g of 1(S)-hydroxy-2-methyl-3-(2-propen-1-yl)-cyclopent-2-ene-4-one, 0.05 g of p-toluene sulfonic acid and 30 ml of petroleum ether (b.p.=35°–75° C.) was refluxed with stirring for 4 hours while azeotropically removing the water of reaction and after cooling the mixture to 0° C., the mixture was stirred and vacuum filtered. The recovered product was washed and dried to obtain 8.7 g of (1R,5S) 6,6-dimethyl-4(R)-[1(S)-2-methyl-4-oxo-3-(2-propen-1-yl)-cyclopent-2-enyloxy]-3-oxabicyclo-(3,1,0)hexan-2-one melting at 104° C. The mother liquors were evaporated to dryness and the residue was crystallized from isopropanol to obtain another 0.12 g of the said product.

EXAMPLE 5

(1R,5S) 6,6-dimethyl-4(R)-[1(S)-2-methyl-4-oxo-3-(2-propen-1-yl)-cyclopent-2-enyloxy]-3-oxabicyclo-(3,1,0)-hexan-2-one In a receptable mounted over a system for azeotropic decantation, a mixture of 25.2 g of 1(S)-hydroxy-2-methyl-3-(2-propen-1-yl)-cyclopent-2-ene-4-one-[(S)-allethrolone], 23.5 g of the lactone of dl cis 2,2-dimethyl-3-(dihydroxymethyl)-cyclopropane-1-carboxylic acid, 0.25 g of p-toluene sulfonic acid and 250 ml of benzene was refluxed with stirring while eliminating by azeotropic decantation the water of reaction for 4 hours. The mixture was cooled and was neutralized with triethylamine. The mixture was evaporated to dryness under reduced pressure and 5 ml of isopropyl ether were added to the residue. The mixture was stirred at 0° C. for one hour and was vacuum filtered. The recovered product was washed and dried to obtain 15.1 g of (1R,5S) 6,6-dimethyl-4(R)-[1(S)-2-methyl-4-oxo-3-(2-propen-1-yl)-cyclopent-2-enyloxy]-3-oxabicyclo-(3,1,0)-hexan-2-one melting at 104° C.

EXAMPLE 6

1(S)-hydroxy-2-methyl-3-(2-propen-1-yl)-cyclopent-2-ene-4-one- or(S) allethrolone A mixture of 82.6 g of the product of Example 4, 826 ml of water and 8.2 ml of aqueous 22° Bé hydrochloric acid was stirred at 20° C. for 72 hours and the pH of the resulting solution was adjusted to 10.5 by addition of aqueous N sodium hydroxide. The mixture was extracted with methylene chloride and the organic phase was dried and evaporated to dryness under reduced pressure to obtain 42.9 g of 1(S)-hydroxy-2-methyl-3-(2-propen-1-yl)-cyclopent-2-ene-4-one with a specific rotation of $[\alpha]_D 20 = +14°$ (c=1.2% in chloroform).

Circular dichroism (dioxane): $\Delta\epsilon = -20$ at 230 nm (max.); $\Delta\epsilon = +3.36$ at 321 nm (max.); $\Delta\epsilon = +3.0$ at 331 nm (max.).

EXAMPLE 7

(R)-allethrolone

A mixture of 82.4 g of the product of Example 3, 824 ml of water and 8.2 ml of aqueous 22° Bé hydrochloric acid was stirred for 72 hours at 20° C. and the pH of the resulting solution was adjusted to 10.5 by addition of aqueous N sodium hydroxide. The mixture was extracted with methylene chloride and the organic phase was dried and evaporated to dryness under reduced pressure to obtain 42.7 g of (R)-allethrolone with a specific rotation of $[60]_D 20 = -14.5°$ (c=1.2% in chloroform).

Circular dichroism (dioxane): $\Delta\epsilon = +20$ at 230 nm (max.); $\Delta\epsilon = -3.36$ at 321 nm (max.); $\Delta\epsilon = -3.0$ at 331 nm (max.).

EXAMPLE 8

(S)-allethrolone

A mixture of 8.3 g of the product of Example 3, 0.83 g of p-toluene sulfonic acid and 42 ml of methanol was stirred at 20° C. for 2 hours and the pH was then adjusted to 7 by addition of sodium carbonate. The mixture was filtered and the filtrate was evaporated to dryness under reduced pressure. The 10 g of residue was chromatographed over silica gel and was eluted with a 7-3 benzene-ethyl acetate mixture to obtain 4.4 g of (S)-allethrolone with a specific rotation of $[\alpha]_D 20 = +14.5°$ (c=1.2% in chloroform).

Circular dichroism (dioxane): $\Delta\epsilon = -20.4$ at 229 nm (max.); $\Delta\epsilon = +3.36$ at 321 nm (max.); $\Delta\epsilon = +3.08$ at 331 nm (max.).

EXAMPLE 9

Lactone of cis 2,2-dimethyl-3S-(dihydroxymethyl)-cyclopropane-1R-carboxylic acid A mixture of 2.76 g of the product of Example 5, 1 ml of aqueous 22° Bé hydrochloric acid and 100 ml of water was stirred for 72 hours and the pH of the solution was adjusted to 10 by addition of aqueous N sodium hydroxide. The basic aqueous phase was extracted with methylene chloride and the organic phase was washed with water, dried and evaporated to dryness under reduced pressure to obtain 1.39 g of (S) allethrolone. The aqueous phase was saturated with ammonium sulfate and was then acidified by addition of hydrochloric acid. The mixture was stirred for one hour and was vacuum filtered. The insoluble gum residue was dissolved in ethyl acetate and the mixture was filtered. The filtrate was evaporated to dryness to obtain 1.32 g of the lactone of cis 2,3-dismethyl-3S-(dihydroxymethyl)-cyclopropane-1R-carboxylic acid.

EXAMPLE 10

(3R, 3aR, 4S, 7R, 7aS)-3-[(1R)-2-methyl-4-oxo-3-(2-propen-1-yl)-cyclopent-2-enyloxy]-tetrahydro-4,7-methano-isobenzofuran-1-one A mixture of 4.3 g of (3R, 3aR, 4S, 7R, 7aS) 3-hydroxy-tetrahydro-4,7-methano-isobenzofuran-1-one of Example 24, 3.9 g of 1-(R,S)-hydroxy-2-methyl-3-(2-propen-1-yl)-cyclopent-2-ene-4-one, 40 mg of p-toluene sulfonic acid and 50 ml of anhydrous benzene was refluxed for 18 hours and was then evaporated to dryness under reduced pressure. The residue was chromatographed over silica gel and was eluted with a 100-2.5 chloroform-acetone mixture to obtain 2.4 g of (3R, 3aR, 4S, 7R, 7aS) 3-[(1R)-2-methyl-4-oxo-3-(2-propen-1-yl)cyclopent-2-enyloxy]-tetrahydro-4,7-methano-isobenzofuran-1-one in the form of an oil.

EXAMPLE 11

(3R, 3aR, 4S, 7R, 7aS) 3-[(1S)-2-methyl-4-oxo-3-(2-propen-1-yl)-cyclopent-2-enyloxy]-tetrahydro-4,7-methano-isobenzofuran-1-one Following the chromatography of Example 10, there were obtained 2.7 g of (3R, 3aR, 4S, 7R, 7aS) 3-[(1S)-2-methyl-4-oxo-3-(2-propen-1-yl)-cyclopent-2-enyloxy]-tetrahydro-4,7-methano-isobenzofuran-1-one in the form of white crystals melting at 148° C.

EXAMPLE 12

(3R, 3aR, 4S, 7R, 7aS) 3-[(1S)-2-methyl-4-oxo-3-(2-propen-1-yl)-cyclopent-2-enyloxy]-tetrahydro-4,7-methano-isobenzofuran-1-one (isomer A) and (3S, 3aS, 4R, 7S, 7aR) 3-[(1S)-2-methyl-4-oxo-3-(2-propen-1-yl)-cyclopent-2-enyloxy]-tetrahydro-4,7-methano-isobenzofuran-1-one (isomer B)

STEP A:
3-hydroxy-tetrahydro-4,7-methano-isolbenzofuran-1-one

A mixture of 30 g of 5-hydroxy-2(5H)-furanone, 150 ml of chloroform, 50 mg of hydroquinone and 35 ml of freshly distilled cyclopentadiene was stirred at 20° C. under an inert atmosphere and stirred for 17 hours at 20°-45° C. The mixture was evaporated to dryness under reduced pressure and the residue was crystallized from an isopropyl ether-petroleum ether mixture to obtain 46.6 g of 3-hydroxy-tetrahydro-4,7-methano-isobenzofuran-1-one melting at ≃103° C.

Analysis: $C_9H_{10}O_3$; molecular weight=166.17, Calculated: %C 65.05, %H 6.06, Found: %C 65.3, %H 6.2.

I.R. Spectrum ($CHCl_3$): 3580 $cm^{-1}$ (OH); 1770 $cm^{-1}$ (C=0).

RMN Spectrum (deuterochloroform): peaks at 6.2–6.22 ppm (ethylenic hydrogens); at 5.18–5.27 ppm (1-hydrogen); at 4.87–4.95 ppm (hydrogen of 1-hydroxyl); at 1.33 to 1.75 ppm (hydrogens of methylene).

STEP B: (3R, 3aR, 4S, 7R, 7aS) 3-[(1S)-2-methyl-4-oxo-3-(2-propen-1-yl)-cyclopent-2-enyloxy]-tetrahydro-4,7-methano-isobenzofuran-1-one (isomer A) and (3S, 3aS, 4R, 7S, 7aR) 3-[(1S)-2-methyl-4-oxo-3-(2-propen-1-yl)-cyclopent-2-enyloxy]-tetrahydro-4,7-methano-isobenzofuran-1-one (isomer B)

A mixture of 33 g of racemic 3-hydroxy-tetrahydro-4,7-methano-isobenzofuran-1-one, 30 g of (S)-allethrolone, 0.18 g of p-toluene sulfonic acid and 200 ml of benzene was refluxed for 4 hours and was evaporated to dryness under reduced pressure. The 60.3 g of residue were chromatographed over silica gel and was eluted with a 100-5 chloroform-actone mixture to obtain 17.4 g of (3R, 3aR, 4S, 7R, 7aS) 3-[(1S)-2-methyl-4-oxo-3-(2-propen-1-yl)-cyclopent-2-enyloxy]-tetrahydro-4,7-methano-isobenzofuran-1-one (isomer A) melting at 148° C. and a specific rotation of $[\alpha]_D^{20} = -8°$ (c=1.5% in benzene) and 13.6 g of (3S, 3aS, 4R, 7S, 7aR)-3-[(1S)-2-methyl-4-oxo-3-(2-propen-1-yl)-cyclopent-2-enyloxy]-tetrahydro-4,7-methano-isobenzofuran-1-one having a specific rotation of $[\alpha]_D^{20} = +42.5°$ (c=1% in benzene).

Isomer A: Analysis: $C_{18}H_{20}O_4$; molecular weight=300.36. Calculated: %C 71.98, %H 6.71, Found: %C 72.0, %H 6.8.

I.R. Spectrum (chloroform): Absorption at 1775 $cm^{-1}$ (lactone); at 1700 $cm^{-1}$ (carbonyl); at 1657 $cm^{-1}$, 1640 $cm^{-1}$ (conjugated ethylenic double bond); at 981–918 $cm^{-1}$ (vinyl).

Circular dichroism (dioxane): $\Delta\epsilon = -18.3$ at 225 nm (max.); $\Delta\epsilon = +2.29$ at 321 nm (max.); $\Delta\epsilon = +2.59$ at 332 nm (max.).

RMN Spectrum (deuterochloroform): peaks at 6.25–6.28 ppm (ethylenic hydrogens of lacetone 5,6); at 5.1 ppm (3-hydrogen of lactone); at 1.33 to 1.75 ppm (hydrogens of 8-$CH_2$ of lactone); at 4.58 (1-hydrogen of allethrolone ring); at 2.07 ppm (hydrogens of 2-methyl of allethrolone ring); at 5.17 to 6.33 ppm (2'-hydrogens of propenyl); at 4.83 to 5.13 ppm (3'-hydrogens of propenyl).

Isomer B: Analysis: $C_{18}H_{20}O_4$; molecular weight=300.36 Calculated: %C 71.98, %H 6.71, Found: %C 71.8, %H 6.7.

I.R. Spectrum (chloroform): absorbtion at 1770 $cm^{-1}$ (carbonyl); at 1706 $cm^{-1}$ (conjugated carbonyl); at 1656–1640 $cm^{-1}$ (conjugated ethylenic double bond); at 982–918 $cm^{-1}$ (vinyl).

Circular dichroism (dioxane): $\Delta\epsilon = -18.4$ at 226 nm (max.); $\Delta\epsilon = +2.9$ at 319 nm (max.); $\Delta\epsilon = +2.63$ at 331 nm (max.).

RMN Spectrum (deuterochloroform): peaks at 6.25–6.28 ppm (5,6 ethylenic hydrogens of lactone); at 5.0 ppm (3-hydrogen of lactone); at 1.33 to 1.75 ppm (hydrogens of 8-$CH_2$ of lactone); at 4.73 (1-hydrogen of allethrolone ring); at 2.03 ppm (hydrogens of 2-methyl of allethrolone; at 5.33–6.33 ppm (2'-hydrogens of propenyl); at 4.83 to 5.13 ppm (3'-hydrogens of propenyl).

EXAMPLE 13

(3S, 3aS, 4R, 7S, 7aR)
3-[(1R)-2-methyl-4-oxo-3-(2-propen-1-yl)-cyclopent-2-enyloxy]-tetrahydro-4,7-methano-isobenzofuran-1-one (isomer D) and (3R, 3aR, 4S, 7R, 7aS)
3-[(1R)-2-methyl-4-oxo-3-(2-propen-1-yl)-cyclopent-2-enyloxy]-tetrahydro-4,7-methano-isobenzofuran-1-one (isomer C)

A mixture of 18.4 g of racemic 3-hydroxy-tetrahydro-4,7-methano-isobenzofuran-1-one, 16 g of (R)-allethrolone, 0.10 g of p-toluene sulfonic acid monohydrate and 100 ml of anhydrous benzene was refluxed for 18 hours and was then evaporated to dryness under reduced pressure. The 31.4 g of residue was chromatographed over silica gel and was eluted with a 100-5 chloroform-acetone mixture to obtain 9.4 g of (3S, 3aS, 4R, 7S, 7aR) 3-[(1R)-2-methyl-4-oxo-3-(2-propen-1-yl)-cyclopent-2-enyloxy]-tetrahydro-4,7-methano-isobenzofuran-1-one (isomer D) in the form of white crystals melting at 148° C. and having a specific rotation of $[\alpha]_D^{20} = +11.5° \pm 1°$ (c=1% in benzene) and 11.7 g of (3R, 3aR, 4S, 7R, 7aS) 3-[(1R)-2-methyl-4-oxo-3-(2-propen-1-yl)-cyclopent-2-enyloxy]-tetrahydro-4,7-methano-isobenzofuran-1-one (isomer C) in the form of a gummy crystal and having a specification of $[\alpha]_D^{20} = -51° \pm 1°$ (c=1% in benzene).

Isomer D: RMN Spectrum (deuterochloroform): peaks at 6.23 ppm (ethylenic hydrogens of lacetone 5,6); at 1.33–1.75 ppm (hydrogens of 8-$CH_2$ of lactone); at 5.0 ppm (3-hydrogen of lactone); at 4.5–4.58 ppm (1-hydrogen of allethrolone ring); at 2.06 ppm (hydrogens of $CH_3$ of allethrolone).

I.R. Spectrum ($CHCl_3$): absorption at 1775 $cm^{-1}$ (carbonyl of lactone); at 1700 $cm^{-1}$ (conjugated carbonyl); at 1657–1640 $cm^{-1}$ (C=C and conjugated).

Circular dichroism (dioxane): In accord with ether of (R) allethrolone, curve practically antipodal to isomer A of Example 12—$\Delta\epsilon = +23.0$ at 225 nm (max.); $\Delta\epsilon = -3.0$ at 320 nm (max.); $\Delta\epsilon = -2.69$ at 332 nm (max.).

Isomer C: Circular dichroism (dioxane): In accord with ether of (R)-allethrolone-curve practically antipodal to isomer B of Example 12—$\Delta\epsilon = -19.1$ at +224 nm (max.); $\Delta\epsilon = -2.88$ at 318 nm (max.); $\Delta\epsilon = -2.59$ at 330 nm (max.).

RMN Spectrum (deuterochloroform): peaks at 6.26 ppm (ethylenic hydrogens of lactone copule); at 1.33–1.75 ppm (hydrogens of 8-$CH_2$ of lactone copule); at 5.0 ppm (1-hydrogen of lactone copule); at 4.7 ppm (1-hydrogen of allethrolone ring); at 2.0 ppm (hydrogen of $CH_3$ of allethrolone ring); at 5.33–6.33 ppm (2'-hydrogen of propenyl); at 4.83–5.1 ppm (3'-hydrogen of propenyl).

I.R. Spectrum ($CHCl_3$): absorbtion at 1770 $cm^{-1}$ (lactone carbonyl); at 1706 $cm^{-1}$ (conjugated carbonyl); at 1656–1640 $cm^{-1}$ (C=C and conjugated).

EXAMPLE 14

(1R, 5S)
6,6-dimethyl-4(R)-[3',3'-dimethyl-butyrolactone-2'-(S)-oxy]-3-oxabicyclo-(3,1,0)-hexan-2-one (compound A) and (1R, 5S)
6,6-dimethyl-4(R)-[3',3'-dimethyl-butyrolactone-2'-(R)-oxy]-3-oxa-bicyclo-(3,1,0)hexane-2-one-(compound B).

A mixture of 7 g of pantolactone. 7.1 g of the lactone of 2,2-dimethyl-3S-(dihydroxymethyl)-cyclopropane-1R-carboxylic acid, 140 mg of p-toluene sulfonic acid and 50 ml of benzene was stirred under an inert atmosphere and was then refluxed for 7¼ hours. The benzene was evaporated at 40° C. under reduced pressure and the residue was chromatographed over silica gel. Elution with an 85-15 benzene-ethyl acetate mixture yielded 2.956 g of (1R, 5S) 6,6-dimethyl-4(R)-[3',3'-dimethylbutyrolactone-2'-(S)-oxy]-3-oxabicyclo-(3,1,0)-hexane-2-one melting at 102°–104° C. (compound A) and then 547 mg of (1R, 5S) 6,6-dimethyl-4(S)-[3',3'-dimethylbutyrolactone-2'-(R)-oxy]-3-oxabicyclo-(3,1,0)hexan-2-one melting at 134° C. and finally 1.654 g of (1R, 5S) 6,6-dimethyl-4(R)-[3',3'-dimethylbutyrolactone-2'-(R)-oxy]-3-oxabicyclo-(3,1,0)-hexan-2-one melting at 120° C. (Compound B).

RMN Spectrum (deuterochloroform): Compound A—peaks at 4.00 ppm (4'-hydrogens of pantolactone); at 4.2 ppm (2'-hydrogen of pantolactone); at ≃5.7 ppm (4-hydrogen of bicyclo (3,1,0)hexanone); at 2–2.1 and 2.22–2.31 ppm (1- and 3-hydrogens of cyclopropyl); at 1.1–1.22 ppm (hydrogens of methyls). Compound B—peaks at 4.0 ppm (4'-hydrogens of pantolactone); at 4.23 ppm (2'-hydrogen of pantolactone); at 5.47 ppm (4-hydrogen of bicyclo (3,1,0) hexanone); at 2.06–2.15 and 2.36–2.45 ppm (1- and 3-hydrogens of cyclopropyl); at 1.12–1.2–1.24 ppm (hydrogens of methyls).

EXAMPLE 15

Racemic mixture of (3S, 3aR, 4S, 7R, 7aS)
3[(1S)-2-methyl-4-oxo-3-(2-propen-1-yl)-cyclopent-2-enyloxy]-tetrahydro-4,7-methano-isobenzofuran-1-one and (3R, 3aS, 4R, 7S, 7aR)
3-[1(S)-2-methyl-4-oxo-3-(2-propen-1-yl)-cyclopent-2-enyloxy]-tetrahydro-4,7-methano-isobenzofuran-1-one.

A mixture of 66 g of racemic 3-hydroxy-tetrahydro-4,7-methano-isobenzofuran-1-one, 60 g of 1(S)-hydroxy-2-methyl-3-(2-propen-1-yl)-cyclopent-2-ene-4-one, 300 mg of p-toluene sulfonic acid and 600 ml of benzene was refluxed for 3 hours and the mixture was neutralized with 4 ml of triethylamine. The mixture was evaporated to dryness and the residue was taken up in isopropyl ether. The mixture was vacuum filtered to recover 23 g of (3R, 3aR, 4S, 7R, 7aS) 3-[1(S)-2-methyl-4-oxo-3-(2-propen-1-yl)-cyclopent-2-enyloxy]-tetrahydro-4,7-methano-isobenzofuran-1-one (compound A) melting at 148° C. The mother liquors were chromatographed over silica gel and elution with a 100-5 chloroform-acetone mixture yielded first 28.8 g of (3S, 3aS, 4R, 7S, 7aR) 3[1(S)-2-methyl-4-oxo-3-(2-propen-1-yl)-cyclopent-2-enyloxy]-tetrahydro-4,7-methano-isobenzofuran-1-one (compound B), then 26 g of compound A and finally 16 g of a mixture of racemic mixture of (3S, 3aR, 4S, 7R, 7aS) 3-[1(S)-2-methyl-4-oxo-3-(2-propen-1-yl)-cyclopent-2-enyloxy]-tetrahydro-4,7-methano-isobenzofuran-1-one and (3R, 3aS, 4R, 7S, 7aR) 3-[1(S)-2-methyl-4-oxo-3-(2-propen-1-yl)-cyclopent-2-enyloxy]-tetrahydro-4,7-methano-isobenzofuran-1-one compounds.

I.R. Spectrum ($CHCl_3$): absorption at 1764 $cm^{-1}$ (γ-lactone); at 1708, 1655 and 1639 $cm^{-1}$ (allethrolone).

RMN Spectrum (deuterochloroform): peaks at 6.17 ppm (5,6-ethylenic hydrogens); at 2.92 to 3.42 ppm (3a, 4,7 and 7a hydrogens); at 1.33–1.48 and 1.55–1.7 ppm (8-hydrogens); at 5.58 to 5.75 ppm (3-hydrogen); at 4.5 to 4.83 ppm (1'-hydrogen of allethrolone); at 2.07 ppm (hydrogens of 2'-methyl of allethrolone); at 5.52 to 6.17 ppm (2-hydrogen of propenyl); at 4.83 to 5.17 ppm (3-hydrogens of propenyl).

EXAMPLE 16

(1R,5S) 6,6-dimethyl-4(R)-[(R)-ethynyl-(3'-phenoxyphenyl)-methoxy]-3-oxabicyclo-(3,1,0)-hexan-2-one (isomer R)

A mixture of 20 g of the lactone of cis 2,2-dimethyl-3S-(dihydroxymethyl)-cyclopropane-1R-carboxylic acid, 30 g of racemic ethynyl-(3'-phenoxyphenyl)-methanol, 200 mg of p-toluene sulfonic acid and 200 ml of benzene was refluxed with stirring for one hour while azeotropically removing the water of reaction and after cooling to 20° C., the mixture was neutralized with triethylamine. The mixture was evaporated to dryness under reduced pressure and the 51 g of brown oil residue was chromatographed under pressure. Elution with a 95-5 benzene-ethyl acetate mixture obtained 10.7 g of (1R,5S) 6,6-dimethyl-4(R)-[(R)-ethynyl-(3'-phenoxyphenyl)-methoxy]-3-oxabicyclo-(3,1,0)-hexan-2-one (isomer R) in the form of an oil.

RMN Spectrum (deuterochloroform): peaks at 1.16-1.25 ppm (hydrogens of geminal methyls); at 5.65 ppm (4-hydrogen); at 2.68-2.7 ppm (hydrogen of ethynyl); at 5.50-5.52 ppm (hydrogen of carbon attached to ethynyl); at 6.8 to 7.50 ppm (hydrogens of aromatic ring); at 1.95-2.03 and 2.1-2.18 ppm (hydrogens of cyclopropyl).

EXAMPLE 17

(1R,5S) 6,6-dimethyl-4(R)-[(S)-ethynyl-(3'-phenoxyphenyl)-methoxy]-3-oxabicyclo-(3,1,0)-hexano-2-one (isomer S)

Following the chromatography under pressure of Example 16, there was obtained 10.4 g of (1R,5S) 6,6-dimethyl-4(R)-[(S)-ethynyl-(3'-phenoxyphenyl)-methoxy]-3-oxabicyclo-(3,1,0)-hexan-2-one (isomer S) in the form of an oil and then 8.4 g of a mixture of the said R and S isomers.

RMN Spectrum (deuterochloroform): isomer S peaks at 1.11 ppm (hydrogens of geminal methyls); at 5.05 ppm (4-hydrogen); at 2.65-2.68 ppm (hydrogen of ethynyl); at 5.41-5.45 ppm (hydrogen of carbon attached to ethynyl); at 2.05 ppm (hydrogens of cyclopropyl).

EXAMPLE 18

(1R,5S) 6,6-dimethyl-4(R)-[3'-methyl-2'(R)-butoxy]-3-oxabicyclo-(3,1,0)-hexan-2-one A mixture of 28 g of the lactone of cis 2,2-dimethyl-3S-(dihydroxymethyl)-cyclopropane-1R-carboxylic acid, 25 ml of racemic 3-methyl-2-butanol, 100 mg of p-toluene sulfonic acid and 100 ml of benzene was refluxed with stirring for 2 hours while azeotropically removing the water of reaction and after cooling the mixture to 20° C., it was neutralized with triethylamine. The mixture was evaporated to dryness under reduced pressure and the 44 g of oil residue was chromatographed over silica gel to obtain 33 g of a mixture of 2 diastereoisomers. The latter was chromatographed over silica gel under pressure and elution with methylene chloride containing 2% of acetonitrile yielded 160 mg of (1R, 5S) 6,6-dimethyl-4(R)-[3'-methyl-2'(R)-butoxy]-3-oxabicyclo-(3,1,0)-hexan-2-one (isomer R) with a melting point of 19°-21° C. and a specific rotation of $[\alpha]_D^{20} = -143° \pm 3.5°$ (c=0.5% in benzene).

RMN Spectrum (deuterochloroform): peaks at 1.15-1.17 ppm (hydrogens of geminal methyls); at 5.25 ppm (4-hydrogen); at 1.07-1.17 ppm (hydrogens of 1'-methyl of propyloxy); at 3.45 to 3.87 ppm (1'-hydrogen of propyloxy); at 0.83 to 0.93 ppm (hydrogens of 2'- and 3'-methyls of propyloxy).

EXAMPLE 19

(1R, 5S) 6,6-dimethyl-4(R)-[3'-methyl-2'-(S)-butoxy]-3-oxabicyclo-(3,1,0)-hexan-2-one After the recovery of isomer A in Example 18, elution was continued to obtain 57 mg of (1R, 5S) 6,6-dimethyl-4(R)-[3'-methyl-2'-(S)-butoxy]-3-oxabicyclo-(3,1,0)-hexan-2-one (isomer S) with a melting point of $\approx 35°$ C. and a specific rotation of $[\alpha]_D^{20} = -121° \pm 3.5°$ (c=0.5% in benzene).

RMN Spectrum (deuterochloroform): peaks at 1.17-1.19 ppm (hydrogens of geminal methyls); at 5.2 ppm (4-hydrogen); at 3.38 to 3.46 ppm (1'-hydrogen of propyloxy); at 0.83-0.95 ppm (hydrogens of 2' and 3'-methyls of propyloxy); at 1.15-1.25 ppm (hydrogens of 1'-methyl).

EXAMPLE 20

(3S, 3aS, 4R, 7S, 7aR) 3-[1(R)-(3'-phenoxyphenyl)-α-methylmethoxy]-tetrahydro-4,7-methano-isobenzofuran-1-one A mixture of 300 mg of (3S, 3aS, 4R, 7S, 7aR) 3-hydroxy-tetrahydro-4,7-methano-isobenzofuran-1-one, 400 mg of 1(R)(3'-phenoxyphenyl)-α-methyl-methanol, 30 mg of p-toluene sulfonic acid and 30 ml of benzene was refluxed for 90 minutes and was then cooled to 20° C. and neutralized with triethylamine. The mixture was evaporated to dryness under reduced pressure and the oil residue was chromatographed under silica gel. Elution with a 9-1 benzene-ethyl acetate mixture yielded 400 mg of (3S, 3aS, 4R, 7S, 7aR) 3-[1(R)-(3'-phenoxyphenyl)-α-methyl-methoxy]-tetrahydro-4,7-methano-isobenzofuran-1-one (product F) melting at 146° C.

RMN Spectrum (deuterochloroform): peaks at 1.3-1.65 ppm (hydrogens of 8—CH$_2$); at 5.83-6.25 ppm (ethylenic hydrogens); at 4.7 ppm (3-hydrogen); at 1.37-1.48 ppm (hydrogens of α-methyl); at 4.58-4.7-4.82-4.93 ppm (1'-hydrogen of alcohol copule); at 6.83-7.5 ppm (hydrogens of aromatic ring).

Circular dichroism (dioxane): Δε=+1.9 at 235 nm (max.); Δε=+0.58 at 257 nm (Inflex.); Δε=+0.77 at 263 nm (max.); Δε=−1.67 at 276 nm (max.); Δε=−2.00 at 281 nm (max.); structure R at the level of

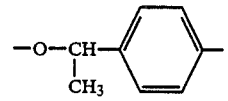

EXAMPLE 21

(3S, 3aS, 4R, 7S, 7aR) 3-[1(S)-(3'-phenoxyphenyl)-α-methylmethoxy]-tetrahydro-4,7-methano-isobenzofuran-1-one A mixture of 300 mg of (3S, 3aS, 4R, 7S, 7aR) 3-hydroxy-tetrahydro-4,7-methano-isobenzofuran-1-one, 400 mg of 1(S)-(3'-phenoxyphenyl)-α-methyl-methanol, 30 mg of p-toluene sulfonic acid and 15 ml of benzene was refluxed with stirring for 90 minutes and after cooling, the mixture was evaporated to dryness under reduced pressure to obtain 900 mg of a thick oil. The latter was chromatographed over silica gel and was eluted with a 95-5 benzene-ethyl acetate mixture to obtain 400 mg of (3S, 3aS, 4R, 7S, 7aR) 3-[1(S)-(3'-phenoxyphenyl)-α-methyl-methoxy]-tetrahydro-4,7-methano-isobenzofuran-1-one melting at 78°-79° C.

I.R. Spectrum (CHCl$_3$): absorption at 1769 cm$^{-1}$ (C=O α-lactone); at 1587-1490 cm$^{-1}$ (aromatic rings); at 1250 cm$^{-1}$ (C—O—C); at 694 cm$^{-1}$ (phenyl ring).

Circular dichroism (dioxane): Δε = +0.8 at 281 nm (max.); Δε = +0.6 at 275 nm (max.); Δε ~ −2.5 to −3 at ≃225 nm (max.).—compatible with S configuration of alcohol moiety.

RMN Spectrum (deuterochloroform): peaks at 6.2 ppm (ethylenic hydrogens); at 1.33-1.75 ppm (hydrogens of 8—CH$_2$); at 5.07 ppm (3-hydrogen); at 1.4-1.5 ppm (hydrogens of α-methyl); at 4.6-4.7-4.8 ppm (hydrogen of carbon attached to α-methyl); at 6.7-7.5 ppm (hydrogens of aromatic ring); at 2.67 to 3.5 ppm (other protons).

EXAMPLE 22

1(S)-hydroxy-2-methyl-3-(2-propen-1-yl)-cyclopent-2-ene-4-one or (S) allethrolone A mixture of 2.7 g of (3R, 3aR, 4S, 7R, 7aS) 3-[(1S)-2-methyl-4-oxo-3-(2-propen-1-yl)-cyclopent-2-enyloxy]-tetrahydro-4,7-methano-isobenzofuran-1-one, 0.25 g of p-toluene sulfonic acid monohydrate, 30 ml of water and 20 ml of dioxane was refluxed for 24 hours and then the solvent was evaporated under reduced pressure. The mixture was neutralized with triethylamine to a pH of 7 and was then evaporated to dryness under reduced pressure. The 2.8 g of residue was chromatographed over silica gel and was eluted with a 1-1 benzene-ethyl acetate mixture containing 0.1% of triethylamine to obtain 1 g of (S) allethrolone, 0.4 g of lactone and 0.7 g of a mixture of (S) allethrolone-lactone. The (S) allethrolone had a specific rotation of $[\alpha]_D^{20}$ = +6.5°±1° (c=1.5% in benzene).

Circular dichroism (dioxane): Δε = −15.7 at 228 nm (max.); Δε = +2.46 at 318-319 nm (max.); Δε = +2.26 at 330 nm (max.).

EXAMPLE 23

1(R)-hydroxy-2-methyl-3-(2-propen-1-yl)-cyclopent-2-ene-4-one or (R)-allethrolone Using the procedure of Example 22, (3R, 3aR, 4S, 7R, 7aS) 3-[(1R)-2-methyl-4-oxo-3-(2-propen-1-yl)-cyclopent-2-enyloxy]-tetrahydro-4,7-methano-isobenzofuran-1-one was reacted to obtain the same yield of (R)-allethrolone with a specific rotation of $[\alpha]_D^{20}$ = −6.5°±1° (c=0.8% in benzene).

Circular dichroism (dioxane): Δε = +17.3 at 228 nm (max.); Δε = −2.92 at 318 nm (max.); Δε = −2.68 at 330 nm (max.).

EXAMPLE 24

(3R, 3aR, 4S, 7S, 7aS)
3-hydroxy-tetrahydro-4,7-methano-isobenzofuran-1-one

A mixture of 12.8 g of (3R, 3aR, 4S, 7R, 7aS) 3-[(1S)-2-methyl-4-oxo-3-(2-propen-1-yl)-cyclopent-2-enyloxy]-tetrahydro-4,7-methano-isobenzofuran-1-one, 1.2 g of p-toluene sulfonic acid monohydrate, 120 ml of water and 60 ml of dioxane was refluxed for 2 hours and was neutralized to a pH of 7 with triethylamine. The mixture was evaporated to dryness under reduced pressure and the residue was chromatographed over silica gel. Elution with a 1-1 benzene-ethyl acetate mixture containing 0.1% of triethylamine yield 5.3 g of (3R, 3aR, 4S, 7R, 7aS) 3-hydroxy-tetrahydro-4,7-methano-isobenzofuran-1-one in the form of white crystals melting at 120° C. and a specific rotation of $[\alpha]_D^{20}$ = +49.5° (c=1% in chloroform).

Analysis: C$_9$H$_{10}$O$_3$; molecular weight =166.17, Calculated: % C 65.05 % H 6.07, Found: % C 65.0 % H 6.1.

Circular dichroism (dioxane): Δε = +2.57 at 218 nm (max.); Δε = −0.015 at 292 nm (max.); Δε = +0.011 at 333 nm (max.); Δε = +0.006 at 345 nm (max.).

I.R. Spectrum (CHCl$_3$): absorption at 3580 cm$^{-1}$ (OH); at 1769-1740 cm$^{-1}$ (C=O).

RMN Spectrum (deuterochloroform): peaks at 6.2 ppm (ethylenic hydrogens); at 5.22-5.23 ppm (3—hydrogen); at 4.75 ppm (hydrogen of hydroxyl); at 1.33-1.73 ppm (hydrogens of 8—CH$_2$); at 2.75-3.52 ppm (other protons).

EXAMPLE 25

(3S, 3aS, 4R, 7S, 7aR)
3-hydroxy-tetrahydro-4,7-methano-isobenzofuran-1-one

A mixture of 1.9 g of (3S, 3aS, 4R, 7S, 7aR) 3-[(1R)-2-methyl-4-oxo-3-(2-propen-1-yl)-cyclopent-2-enyloxy]-tetrahydro-4,7-methano-isobenzofuran-1-one, 0.2 g of p-toluene sulfonic acid monohydrate, 20 ml of water and 20 ml of dioxane was refluxed for 6 hours and was neutralized to pH of 7 with triethylamine. The mixture was evaporated to dryness under reduced pressure and the residue was chromatographed over silica gel. Elution with a 1-1 benzene-ethyl acetate mixture containing 0.1% of triethylamine yielded 650 mg of (3S, 3aS, 4R, 7S, 7aR) 3-hydroxy-tetrahydro-4,7-methano-isobenzofuran-1-one melting at 120° C. and having a specific rotation of $[\alpha]_D^{20}$ = −47.5°±2.5° (c=1% in chloroform).

RMN Spectrum (deuterochloroform): peaks at 6.23 ppm (ethylenic hydrogens); at 5.25 ppm (3—hydrogen); at 4.9 ppm (hydrogen of —OH); at 1.35-1.5 and 1.6-1.75 ppm (hydrogens of 8—CH$_2$); at 2.83 to 3.58 ppm (other protons).

EXAMPLE 26

Racemic mixture of (3S, 3aR, 4S, 7R, 7aS)
3-hydroxy-tetrahydro-4,7-methano-isobenzofuran-1-one and (3R, 3aS, 4R, 7S, 7aR)
3-hydroxy-tetrahydro-4,7-methano-isobenzofuran-1-one A mixture of 15 g of the mixture obtained in Example 15, 75 ml of dioxane, 150 ml of water and 1.5 g of p-toluene sulfonic acid was refluxed for 2 hours and after cooling the mixture, the pH was adjusted to 7-8 with triethylamine. The mixture was evaporated to dryness under reduced pressure and the residue was chromatographed over silica gel. Elution with a 1-1 benzene-ethyl acetate mixture containing 0.1% of triethylamine yielded 4.85 g of racemic mixture of (3S, 3aR, 4S, 7R, 7aS) 3-hydroxy-tetrahydro-4,7-methano-isobenzofuran-1-one and (3R, 3aS, 4R, 7S, 7aR) 3-hydroxy-tetrahydro-4,7-methano-isobenzofuran-1-one with a melting point of 103° C.

RMN Spectrum (deuterochloroform): peaks at 6.2 ppm (ethylenic hydrogens); at 5.22 ppm (3-hydrogen); at 1.33-1.48 and 1.55-1.7 ppm (hydrogens of 8—CH$_2$); at 4.67 ppm (hydrogen of OH); at 2.75 to 3.5 ppm (other protons). By circular dichroism at 218 nm of lactone chromophore, it was ascertained that the product was racemic.

EXAMPLE 27

(S) 1-(3-phenoxyphenyl)-prop-2-yn-1-ol

A mixture of 10.4 g of (1R, 5S) 6,6-dimethyl-4(R)-[(S)-ethynyl-(3'-phenoxy-phenyl)-methoxy]-3-oxabicyclo-(3,1,0)-hexan-2-one, 1 g of p-toluene sulfonic acid, 80 ml of water and 80 ml of dioxane was refluxed for 2 hours and was evaporated to dryness under reduced pressure. The residue was added to water and the mixture was stirred and was extracted with isopropyl ether. The organic phase was subjected to the usual treatment and was evaporated to dryness under reduced pressure. The 6 g of residue was chromatographed over silica gel and was eluted with a 7–3 benzene ethyl acetate mixture to obtain 5.1 g of (S) 1-(3-phenoxyphenyl)-prop-2-yn-1-ol with a specific rotation of $[\alpha]_D^{20} = +10.5°$ (c=0.63% in benzene).

RMN Spectrum (deuterochloroform): peaks at 2.30 ppm (hydrogen of —OH); at 2.61–2.66 ppm (ethylenic hydrogens); at 5.44–5.50 ppm (hydrogen of carbon attached to ethynyl); at 6.91–7.0 ppm (hydrogens of aromatic ring).

Circular dichroism (dioxane): $\Delta\epsilon = +1.9$ at 215 nm (max.); $\Delta\epsilon = +0.02$ at 272 nm (max.); $\Delta\epsilon = -0.01$ at 276 nm (max.); $\Delta\epsilon = +0.04$ at 278 nm (max.); $\Delta\epsilon = -0.03$ at 283 nm (max.).

EXAMPLE 28

(R) 1-(3-phenoxyphenyl)-prop-2-yn-1-ol

Using the procedure of Example 27, 10.6 g of (1R, 5S) 6,6-dimethyl-4(R)-[(R)-ethynyl-(3'-phenoxyphenyl)-methoxy]-3-oxabicyclo-(3,1,0)-hexan-2-one were reacted to obtain 5.6 g of (R) 1-(3-phenoxyphenyl)-prop-2-yn-1-ol with a specific rotation of $[\alpha]_D^{20} = -16°$ (c=1% in benzene).

RMN Spectrum (deuterochloroform): peaks at 2.58–2.62 ppm (acetylenic hydrogen); at 2.66 ppm (hydrogen of —OH); at 5.36–5.40 ppm (hydrogen on carbon attached to ethynyl); at 6.83–7.50 (hydrogens of aromatic ring).

EXAMPLE 29

3-methyl-2-(S)-butanol

A mixture of 16.9 g of (1R, 5S) 6,6-dimethyl-4(R)-[3-methyl-2(S)-butoxy]-3-oxabicyclo-(3,1,0)-hexan-2-one, 70 ml of 2 N hydrochloric acid and 8.5 ml of acetone was heated at 50° C. with stirring for 16 hours and the mixture was cooled to 20° C. and extracted with ether. The combined ether extracts were washed with 2 N ammonium hydroxide solution, with water until the wash waters were neutral, dried and evaporated to dryness under reduced pressure. The oily product of 3-methyl-2(S)-butanol was distilled to obtain 1.7 g of an oil with a boiling point of 108° C. at 760 mmHg and a specific rotation of $[\alpha]_D^{20} = +3° \pm 1°$ (c=1.0% in ethanol).

RMN Spectrum (deuterochloroform): peaks at 1.08–1.2 ppm (hydrogens of 1-methyl); at 1.5 ppm (hydrogen of OH); at 3.58 ppm (2-hydrogen); at 1.58 ppm (3-hydrogen); at 0.85–0.95 ppm (hydrogens of 3- and 4-methyl).

EXAMPLE 30

3-methyl-2(R)-butanol

A mixture of 16 g of (1R, 5S) 6,6-dimethyl-4(R)-[3'-methyl-2'(R)-butoxy]-3-oxabicyclo-(3,1,0)-hexan-2-one, 70 ml of 2 N hydrochloric acid and 10 ml of acetone was stirred at 50° C. for 16 hours and was then cooled to 20° C. and extracted with ether. The combined ether extracts were washed with 2 N ammonium hydroxide and then with water until the wash waters were neutral and dried and evaporated to dryness under reduced pressure. The 7 g of oil was distilled to obtain 1.5 g of 3-methyl-2(R)-butanol in the form of an oil with a boiling point of 110° C. at 760 mm Hg and with a specific rotation of $[\alpha]_D^{20} = -4.5° \pm 1°$ (c=1.3% in ethanol).

RMN Spectrum (deuterochloroform): peaks at 1.1–1.2 ppm (hydrogens of 1-methyl); at 1.67 ppm (hydrogen of OH); at 3.58 ppm (2-hydrogen); at 1.67 ppm (3-hydrogen); at 0.85–0.97 ppm (hydrogens of 3- and 4-methyls)

EXAMPLE 31

2(S)-hydroxy-3,3-dimethyl-butyrolactone or (S)-pantolactone

A mixture of 20 g of (1R, 5S) 6,6-dimethyl-4(R)-[3',3'-dimethylbutyrolactone-2'(S)-oxy]-3-oxabicyclo-(3,1,0)-hexan-2-one, 100 ml of water, 100 ml of dioxane and 1 g of p-toluene sulfonic acid monohydrate was refluxed with stirring for 2 hours and after cooling the mixture to room temperature, 100 ml of water were added thereto. The mixture was concentrated under reduced pressure to about 50 ml and was then saturated with sodium chloride and was extracted with methylene chloride. The organic phase was dried and then evaporated to dryness at 40° C. under reduced pressure to obtain a white product which was a mixture of (S)-pantolactone and (1R, 5S) 6,6-dimethyl-4(R)-hydroxy-3-oxabicyclo-(3,1,0)-hexan-2-one (product A). The latter was dissolved in 40 ml of refluxing water and the solution was cooled to room temperature. Crystallization was induced by addition of a few crystals of product A and the mixture was vacuum filtered. The filter was washed with water and the filtrate was evaporated to dryness. The residue was treated as before and was cooled to 0° to 5° C. for 2 hours to recover more product A. The filtrate was then evaporated to dryness and the residue was chromatographed over a silica gel. Elution with a 6-4-toluene-ethyl acetate mixture yielded 7 g of white crystals containing product A. 6 g of the product were dissolved in 50 ml of water and 2 ml of ethanol and 25 ml of aqueous sodium bisulfite solution were added thereto. The mixture was energetically stirred at room temperature for 2 hours and was then saturated with sodium chloride and extracted with ethyl acetate. The organic phase was dried and evaporated to dryness under reduced pressure at 40° C. to obtain 4.5 g of product which was sublimated at 90° C. at 0.1 mm Hg to obtain 2.7 g of (S)-pantolactone melting at ≈90° C. and having a specific rotation of $[\alpha]_D^{20} = +47.5° \pm 1°$ (c=2% in water).

RMN Spectrum (deuterochloroform): peaks at 1.08–1.22 ppm (hydrogens of geminal methyls); at ∼3.77 ppm (hydrogen of —OH); at 3.98 ppm (hydrogens of 4-methylene of cyclopentyl); at 4.18 ppm (2-hydrogen of cyclopentyl).

EXAMPLE 32

2(R)-hydroxy-3,3-dimethyl-butyrolactone or (R)-pantolactone

A mixture of 9 g of (1R, 5S) 6,6-dimethyl-4(R)-[3',3'-dimethyl-butyrolactone-2'(R)-oxy]-3-oxabicyclo-(3,1,0)-hexane-2-one, 90 ml of methanol and 85 mg of p-toluene sulfonic acid monohydrate was refluxed with stirring for 2 hours and was then evaporated to dryness under reduced pressure. The residue was chromatohgraphed over silica gel and was eluted with a 6-4 toluene-ethyl acetate mixture to obtain 1.3 g of yellow crystals which were sublimated at 90° C. at 0.1 mm Hg to obtain 1 g of (R)-pantolactone in the form of hydroscopic white crystals melting at 89° C. and having a specific rotation of $[\alpha]_D^{20} = -50° \pm 1°$ (c=1.96% in water).

EXAMPLE 33

(3R, 3aR, 4S, 7R, 7aS) 3-[(1'R), (2'S), (5'R)-2'-isopropyl-5'-methylcyclohexanoxy]-tetrahydro-4,7-methano-isobenzofuran-1-one A mixture of 1.66 g of (3R, 3aR, 4S, 7R, 7aS) 3-hydroxy-tetrahydro-4,7-methano-isobenzofuran-1-one, 2.34 g of methol, 50 mg of p-toluene sulfonic acid and 42 ml of benzene was refluxed with stirring for 90 minutes and was then cooled to room temperature and evaporated to dryness under reduced pressure. The 4.41 g of oil was chromatographed over silica gel and was eluted with 95-5 -benzene-ethyl acetate mixture to obtain 2.76 g of (3R, 3aR, 4S, 7R, 7aS) 3-[(1'R), (2'S), (5'R)-2'-isopropyl-5'-methylcyclohexanoxy]-tetrahydro-4,7-methano-isobenzofuran-1-one melting at 54° C. and having a specific rotation of $[\alpha]_D^{20} = -120° \pm 2°$ (c=1% in benzene) and 92 mg of isomer S melting at 100° C.

I.R. Spectrum (CHCl3): absorption at 1769 cm$^{-1}$ (max.). and 1760 cm$^{-1}$ (shoulder) (carbonyl of γlactone); at 1390 cm$^{-1}$ (geminal methyls); at 1117 cm$^{-1}$ (C-O-C).

RMN Spectrum (deuterochloroform): peaks at 068–0.8–0.92 ppm (hydrogens of methyls of isopropyl); at 0.88–0.97 ppm (hydrogens of methyl of menthol); at 2.67–3.67 ppm (1'-hydrogen of methanol and 3a-, 4-, 7 and 7a hydrogens of lactone); at 5.03–5.06 ppm (3-hydrogen of lactone); at 6.22 ppm (ethylenic hydrogens).

Circular dichroism (dioxane): Δε=+2.3 at 217 nm (max.).

EXAMPLE 34

3R, 3aR, 4S, 7R, 7aS) 3-[(1'R), (2'S), (5'R) 2'-isopropyl-5'-methylcyclohexanoxy]-tetrahydro-4,7-methano-isobenzofuran-1-one (product R) and (3R, 3aR, 4S, 7R, 7aS) 3-[(1'S), (2'R), (5'S)-2'-isopropyl-5'-methylcyclohexanoxy]-tetrahydro-4,7-methano-isobenzofuran-1-one(Product S)

A mixture of 6.65 g of (3R, 3aR, 4S, 7R, 7aS) 3-hydroxy-tetrahydro-4,7-methano-isobenzofuran-1-one, 9.37 g of racemic methanol, 200 mg of p-toluene sulfonic acid monohydrate and 170 ml of benzene was refluxed for 2 hours and was evaporated to dryness at 40° C. under reduced pressure to obtain 16.17 g of a brown oil. The latter was chromatographed over silica gel and was eluted with a 95-5benzene-ethyl acetate mixture and then a second time with a 98-2 benzene-ethyl acetate mixture to obtain 3.58 g of product R in the form of a white product melting at 53° C. and a specific rotation of $[\alpha]_D^{20} = -113.5° \pm 3°$ (C=0.6 6% in benzene), 4.25 g of product S in the form of a thick oil with a specific rotation of $[\alpha]_D^{20} = -74° \pm 3°$ (c=0.3% in benzene) and 0.57 g of a white wax which was a mixture of products R and S.

RMN Spectrum (deuterochloroform): Product R—peaks at 0.7–0.82–0.93 ppm (hydrogens of methyls of isopropyl); at 0.88–0.97 ppm (hydrogens of methyl); at 5.05–5.07 ppm (3-hydrogen of lactone); at 6.23 ppm (ethylenic hydrogens); at 2.67–3.67 ppm (1-hydrogen of menthol and 4-, 3a-, 7 and 7a-hydrogens of lactone). Product S - peaks at 0.75–0.87–0.98 ppm (hydrogens of methyls of isopropyl); at 0.92–0.87 ppm (hydrogens of methyl); at 4.92–4.95 ppm (3-hydrogen of lactone); at 6.23 ppm (ethylenic hydrogens).

EXAMPLE 35

(1R) (2S) (5R) 2-isopropyl-5-methyl-cyclohexanol

A mixture of 1.78 g of (3R, 3aR, 4S, 7R, 7aS) 3-[(1'R), (2'S), (5'R) 2'-isopropyl-5'-methylcyclohexanoxy]-tetrahydro-4,7-methano-isobenzofuran-1-one, 300 mg of p-toluene sulfonic acid monohydrate, 25 ml of water and 40 ml of dioxane was refluxed with stirring for one hour and 100 ml of water were added thereto. The dioxane was distilled at 40° C. under reduced pressure and the mixture was extracted with ether. The ether phase was washed with water, dried and evaporated to dryness under reduced pressure to obtain 1.12 g of oil. The latter was chromatographed over silica gel and was eluted with a 95-5 benzene-ethyl acetate mixture to obtain 750 mg of (1R) (2S) (5R) 2-isopropyl-5-methyl-cyclohexanol melting at <50° C. and having a specific rotation of $[\alpha]_D^{20} = -49° \pm 2.5°$ (c=0.7% in ethanol).

I.R. Spectrum (CHCl3): absorption at 1370 cm$^{-1}$ (geminal methyls); at 3595 and 3610 cm$^{-1}$ (alcohol group).

EXAMPLE 36

(1R, 5S) 6,6-dimethyl-4(R)-[(1'R), (2'S), (5'R) 2'-isopropyl-5'-methylcyclohexanoxy]-3-oxabicyclo-(3,1,0)-hexan-2-one (product R) and (1R, 5S) 6,6-dimethyl-4(R)-[(1'S), (2'R), (5'S) 2'-isopropyl-5'-methylcyclohexanoxy]-3-oxabicyclo-(3,1,0)-hexan-2-one (product S).

A mixture of 7.3 g of (1R, 5S) 6,6-dimethyl-4(R)-hydroxy-3-oxabicyclo-(3,1,0)-hexa-2-one, 7,8 g of racemic menthol, 100 mg of p-toluene sulfonic acid and 100 ml of benzene was refluxed with stirring for 90 minutes and was then cooled to room temperature. 2 ml of triethylamine were added to the mixture to neutralize it and the mixture was evaporated to dryness under reduced pressure. The 15.7 g of colorless oil was chromatographed over silica gel and was eluted with a 98-2 methylene chloride-acetonitrile mixture to obtain 5.74 g of product R melting at 83° C. and having a specific rotation of $[\alpha]_D^{20} = -180° \pm 2.5°$ (c=1.1% in benzene) and 5.87 g of product S in the form of an oil with a specific rotation of $[\alpha]_D^{20} = -53° \pm 2.5°$ (c=0.42% in benzene).

I.R. Spectrum (CHCl3): Product R-absence of —OH and absorption at 1385 cm$^{-1}$ (geminal methyls) and at 1795 (max.) and 1748 cm$^{-1}$ (shoulder) (C=O of γ-lactone). Product S - absence of OH and absorption at 1385 cm$^{-1}$ (geminal methyls) and at 1795 (max.) and 1748 cm$^{-1}$ (C=O of γlactone)

RMN Spectrum (deuterochloroform): Product R - peaks at 2.0 ppm (1- and 5- hydrogens of lactone copule); at 1.15–1.18 ppm (hydrogens of methyls of lactone copule); at 5.35 ppm (4-hydrogen of lactone copule); at 3.58 ppm (1-hydrogen of menthol); at 0.82–0.99 ppm (hydrogens of 5-methyl of menthol); at 0.75–0.99 ppm (hydrogens of methyls of isopropyl). Product S - peaks at 2.0 ppm (1- and 5- hydrogens of lactone copule); at 1.17–1.18 ppm (hydrogens of methyls of lactone copule); at 5.18 ppm (4-hydrogen of lactone copule); at 3.43 ppm (1-hydrogen of menthol); at 0.75–0.98 ppm (hydrogens of 5-methyl of menthol); at 0.75–0.82 ppm (hydrogens of methyls and isopropyl).

Circular dichroism (dioxane): Product R - $\Delta\epsilon = -3.65$ at 224 nm (max.), Product S - $\Delta\epsilon = -3.20$ at 224–225 nm (max.).

EXAMPLE 37

(1R) (2S) (5R) 2-isopropyl-5-methyl-cyclohexanol

A mixture of 1 g of (1R, 5S) 6,6-dimethyl-4(R)-[(1'R), (2'S), (5'R) 2'-isopropyl-5'-methyl-cyclohexanoxy]-3-oxabicyclo-(3,1,0)-hexan-2-one, 10 ml of water, 10 ml of dioxane and 100 mg of p-toluene sulfonic acid was refluxed with stirring for 2 hours and the mixture was distilled to remove a maximum of dioxane. The mixture was diluted with water and was extracted with isopropyl ether. The organic phase was dried and evaporated to dryness under reduced pressure to obtain 430 mg of oil. The latter was chromatographed over silica gel and was eluted with a 7-3 cyclohexane-ethyl acetate mixture to obtain 350 mg of (1R), (2S), (5R) 2-isopropyl-5-methyl-cyclohexanol idential to natural menthol. The product melted at <50° C. and had a specific rotation of $[\alpha]_D^{20} = -54.5° \pm 1°$ (c=2% in ethanol).

EXAMPLE 38

(1S), (2R), (5S) 2-isopropyl-5-methyl-cyclohexanol

A mixture of 5 g of (1R, 5S) 6,6-dimethyl-4(R)-[(1'S) (2'R) (5'S) 2'-isopropyl-5'-methylcyclohexanoxy]-3-oxabicyclo-(3,1,0)-hexan-2-one, 25 ml of dioxane, 25 ml of water and 100 mg of p-toluene sulfonic acid was refluxed with stirring for 2 hours and was distilled under reduced pressure to remove a maximum of dioxane. The mixture was diluted with water and was extracted with isopropyl ether. The organic phase was dried and evaporated to dryness under reduced pressure to obtain 4.8 g of an oil. The latter was chromatographed over silica gel to obtain 1.7 g of (1S) (2R) (5S) 2-isopropyl-5-methyl-cyclohexanol melting at <50° C. and having a specific rotation of $[\alpha]_D^{20} = +46.5° \pm 2.5°$ (c=0.35% in ethanol).

Various modifications of the products and processes of the invention may be made without departing from the spirit or scope thereof and it should be understood that the invention is intended to be limited only as defined in the appended claims.

We claim:

1. A compound selected from the group consisting of (1R,5S) 6,6-dimethyl-4(R)-[(1'R), (2'S), (5'R) 2'-isopropyl-5'-methylcyclohexanoxy]-3-oxabicyclo-(3,1,0)-hexan-2-one and (1R, 5S) 6,6-dimethyl-4(R)-[(1'S), (2'R), (5'S) 2'-isopropyl-5'-methylcyclohexanoxy]-3-oxabicyclo-(3,1,0)-hexan-2-one.

* * * * *